(12) United States Patent
Engelhardt et al.

(10) Patent No.: US 6,677,596 B2
(45) Date of Patent: Jan. 13, 2004

(54) METHOD AND APPARATUS FOR THE DETECTION OF FLUORESCENT LIGHT IN CONFOCAL SCANNING MICROSCOPY

(75) Inventors: Johann Engelhardt, Bad Schoenborn (DE); Juergen Hoffmann, Wiesbaden (DE)

(73) Assignee: Leica Microsystems Heidelberg GmbH, Mannheim (DE)

( * ) Notice: Subject to any disclaimer, the term of this patent is extended or adjusted under 35 U.S.C. 154(b) by 160 days.

(21) Appl. No.: 09/948,297

(22) Filed: Sep. 6, 2001

(65) Prior Publication Data

US 2002/0027202 A1 Mar. 7, 2002

(30) Foreign Application Priority Data

Sep. 7, 2000 (DE) .......................... 100 44 308

(51) Int. Cl.[7] .................................. G01J 3/28
(52) U.S. Cl. .................. 250/458.1; 250/459.1
(58) Field of Search .................. 250/458.1, 459.1, 250/461.1, 461.2; 356/124, 239.2

(56) References Cited

U.S. PATENT DOCUMENTS

| | | | |
|---|---|---|---|
| 5,034,613 A | | 7/1991 | Denk et al. ............... 250/458.1 |
| 5,117,466 A | * | 5/1992 | Buican et al. ............... 382/133 |
| 5,304,810 A | * | 4/1994 | Amos ....................... 250/458.1 |
| 5,777,732 A | | 7/1998 | Hanninen et al. ........... 356/318 |
| 5,814,820 A | * | 9/1998 | Dong et al. ............... 250/458.1 |
| 6,134,002 A | * | 10/2000 | Stimson et al. ............. 356/326 |
| 6,169,289 B1 | * | 1/2001 | White et al. ............... 250/458.1 |
| 6,259,104 B1 | * | 7/2001 | Baer ........................ 250/492.2 |
| 6,262,423 B1 | | 7/2001 | Hell et al. ................ 250/458.1 |
| 6,369,928 B1 | * | 4/2002 | Mandella et al. ........... 359/204 |
| 6,525,862 B2 | * | 2/2003 | Fisher et al. ................ 359/278 |

FOREIGN PATENT DOCUMENTS

| | | |
|---|---|---|
| DE | 4437896 | 5/1996 |
| DE | 19653413 | 6/1998 |
| DE | 4414940 | 7/1998 |
| EP | 0753779 | 1/1997 |
| WO | WO 00/37984 A2 * | 6/2000 ............ G02B/21/00 |

OTHER PUBLICATIONS

In J.B. Pawley "Handbook of biological confocal Microscopy", 1995, Denk et al. " Two–photon molecular excitation in laser–scanning microscopy" 1995, pp. 445 to 448.

* cited by examiner

Primary Examiner—Constantine Hannaher
Assistant Examiner—Otilia Gabor
(74) Attorney, Agent, or Firm—Davidson, Davidson & Kappel, LLC

(57) ABSTRACT

A method for detection of fluorescent light in scanning microscopy includes dividing an illuminating light beam into a plurality of partial illuminating beams so as to illuminate multiple specimen regions simultaneously. Fluorescing materials in a specimen region are excited via multi-photon excitation. Operating parameters of the light source are adapted for optimum fluorescent photon yield to the properties of the fluorescing material in the specimen region. Fluorescent light of the specimen regions is detected simultaneously.

17 Claims, 2 Drawing Sheets

METHOD AND APPARATUS FOR THE DETECTION OF FLUORESCENT LIGHT IN CONFOCAL SCANNING MICROSCOPY

CROSS REFERENCE TO RELATED APPLICATIONS

This invention claims priority of the German patent application 100 44 308.7 which is incorporated by reference herein.

FIELD OF THE INVENTION

The present invention concerns a method for the detection of fluorescent light in scanning microscopy. Moreover, the invention concerns an apparatus for the detection of fluorescent light.

BACKGROUND OF THE INVENTION

Methods and apparatuses of the generic type have been known from practical use for some time. In scanning microscopy, a specimen is illuminated with a light beam in order to detect the reflected and/or fluorescent light emitted by the specimen. In multi-photon scanning microscopy, the fluorescence photons detected are attributable to a multi-photon excitation process in which the transition from one state of a fluorochrome into the excited state is accomplished by simultaneous absorption of multiple photons. The probability of an N-photon transition depends on the Nth power of the excitation light output of the illuminating light. To achieve high light outputs, the exciting light used for illumination is usually pulsed.

Reference is made, merely by way of example, to U.S. Pat. No. 5,034,613 and DE 44 14 940, which disclose confocal scanning microscopes in which a specimen is excited with a focused light beam; in this instance, two-photon transitions are accomplished with pulsed light. The pulse durations of the individual pulses are femtoseconds or picoseconds.

The generic methods and apparatuses are, however, very inefficient in terms of attainable fluorescent photon yield; there are various reasons for this. On the one hand, the fluorescent photon yield cannot be raised arbitrarily by increasing the illuminating light output. As soon as the saturation output of the fluorescent markers is reached, all the fluorescent markers are excited to fluoresce with one laser pulse. A further increase in illumination output would then have a disadvantageous effect in terms of the bleaching behavior of the fluorescent markers, and would entail a thermal load on the specimen. Further remarks on two-photon excitation of fluorescing specimens are made in the article "Two-Photon Molecular Excitation in Laser Scanning Microscopy," by W. Denk, D. W. Piston, and W. W. Webb, in Handbook of Biological Confocal Microscopy, 1995, ed. J. B. Pawley, 445–458.

Also known per se, from DE 196 53 413 as well as EP 0 753 779 and DE 44 37 896 C1, are arrangements in which, by means of a rotating micro-lens disk or a reflection disk, a specimen is illuminated with exciting light at approximately 20 to 50 specimen points simultaneously.

SUMMARY OF THE INVENTION

It is therefore the object of the invention to provide a method so that the fluorescent photon yield of the fluorescing materials that are excited to fluoresce by multi-photon excitation is optimized or increased in order to enable optimum specimen detection.

The above object is accomplished by a method for the detection of fluorescent light in scanning microscopy comprising the steps of:
  exciting fluorescing materials in a specimen region by means of multi-photon excitation,
  adapting operating parameters of a light source for optimum fluorescent photon yield to the properties of the fluorescing material in the specimen region, wherein the light source causes multi-photon excitation,
  illuminating multiple specimen regions simultaneously, and
  detecting fluorescent light of the specimen regions simultaneously.

It is a further object of the invention to provide an apparatus by which the fluorescent photon yield of the fluorescing materials that are excited to fluoresce by multi-photon excitation is optimized or increased in order to enable optimum specimen detection.

The object is accomplished by an apparatus for the detection of fluorescent light comprising:
  a scanning microscope with a light source for illuminating at least one specimen region,
  means for exciting fluorescing materials in the at least one specimen region by means of multi-photon excitation,
  means for adapting operating parameters of the light source for optimum fluorescent photon yield to the properties of the fluorescing material in the specimen region, wherein the light source causes multi-photon excitation,
  means for illuminating multiple specimen regions simultaneously, and
  means for detecting fluorescent light of the specimen regions simultaneously.

What has been recognized according to the present invention is firstly that the fluorescent photon yield of the fluorescent light of the fluorescent excitation induced by means of multi-photon excitation processes depends on several influencing variables. For example, the properties of the light source causing the multi-photon excitation, the system parameters of the confocal scanning microscope, and the properties of the fluorescing materials are critical. Only when all the influences affecting the fluorescent photon yield are matched and adapted to one another can optimized fluorescent excitation and fluorescent light detection be accomplished.

The lifetime of the excited states of the fluorescing materials is provided for as a possible property of the fluorescing materials to which the operating parameters of the light source causing the multi-photon excitation and/or the system parameters of the confocal microscope could be adapted. Also provided for is an adaptation to the effective cross section of the excitation of the fluorescing materials, to the excitation and/or emission wavelength, and/or an adaptation to the bleaching behavior of the fluorescing materials. These are thus the most important properties of the fluorescing materials to which the light source causing the multi-photon excitation, and the system parameters of the confocal scanning microscope, are to be adapted.

A plurality of variant methods, which will be discussed in more detail below, are provided for modifying the operating parameters of the light source causing the multi-photon excitation.

For one, the output of the light source could be correspondingly adjusted. In this context, the output of the light source would need to be made greater than or equal to the output which corresponds to the saturation output of the fluorescing materials. In confocal scanning microscopy in particular, the saturation output of the fluorescing materials depends on the illumination pattern used for multi-photon excitation of the fluorescing materials, since with increasing illumination volume, the light output to be introduced into the confocal scanning microscope correspondingly increases.

For optimum excitation of the fluorescing materials, the pulse duration of the light emitted by the light source could moreover be adjusted correspondingly. To influence the pulse duration of the light emitted by the light source, a prechirp unit such as is known, for example, from DE 44 37 896 C1 could be used. With this prechirp unit, in particular, light pulses that have experienced a pulse widening as a result of interactions with optical components such as, e.g. glass fibers or lenses, are compressed back to their original pulse duration. This prechirp unit could, however, in particularly advantageous fashion, be used to influence the pulse duration of the light emitted by the light source, in order to optimize the fluorescent photon yield of the fluorescing materials.

In particularly advantageous fashion, provision is made for the pulse repetition rate of the light emitted by the light source to be correspondingly adjusted. In particular, the pulse repetition rate of the light emitted from the light source is to be adjusted, or optionally varied, as a function of the lifetime of the excited states of the fluorescing materials and on the basis of their saturation behavior. Pulse repetition rates of 75 to 100 MHz are usually used for two-photon excitations of fluorescing materials; the use of pulse repetition rates in ranges from kHz to GHz can be useful for optimum fluorescent photon yield.

A modification of the pulse repetition rate could be achieved, in the context of mode-coupled light sources, by the fact that the resonator length of the light source is modified. A decrease in the resonator length would yield an increase in the pulse repetition rate; this can be achieved, for example, with a titanium:sapphire laser. A resonator length in the centimeter range would yield a pulse repetition rate of a few GHz. A corresponding increase in the resonator length would correspondingly lower the pulse repetition rate. Alternatively, a multiplication of the pulse repetition rate, in the context of actively mode-coupled light sources, could be achieved by having several pulses circulate simultaneously in the resonator. For this purpose, the active mode coupling control system would need to be set appropriately so as thereby to achieve, for example, an eight-fold increase in the pulse repetition rate.

If optimization of the fluorescent photon yield of the fluorescing materials is to be brought about by selection of a suitable pulse repetition rate, this generally requires selecting a specific type of light source having pulse repetition rates that lie in the desired range.

For example, a pulsed laser with Q-switching could be used as the light source. In a laser of this kind, generation of the light pulses is achieved by a corresponding Q-switching system, which in turn can be modified over a specific range so that the pulse repetition rate of this type of light source can be adapted to the excitation properties of the fluorescing materials by varying the Q-switching system as well.

In addition, mode-coupled laser systems could be used as the light source; in particular, titanium:sapphire lasers could be utilized. If the light output necessary for optimum excitation of the fluorescing materials is greater than the light output that mode-coupled laser systems usually provide, a regenerative amplifier could be arranged downstream from the mode-coupled laser system.

A semiconductor laser could also be used as the light source for multi-photon excitation of fluorescing materials. This semiconductor laser could be caused to pulse by gain switching. The pulse repetition rate of the semiconductor laser can thereby be adjusted from the Hz range into the GHz range.

An alternative light source could be a flash lamp-pumped laser system, which substantially exhibits pulse repetition rates that substantially correspond to the frequency of the flash lamp.

In particularly advantageous fashion, an OPO (optically parametric oscillator) or OPA (optically parametric amplifier) could be used. With these illumination systems, it is particularly advantageous that the wavelength and pulse repetition rate of the emitted light are continuously variable, thus making possible, for example, an almost ideal adaptation to the absorption wavelength region of the fluorescing materials.

In terms of optimization of the fluorescent photon yield of the fluorescing materials, with regard to the system parameters of the confocal scanning microscope, on the one hand the dynamic range of the detector system and/or on the other hand the pixel integration time of the detector system could be correspondingly adjusted. Also correlated herewith, in particular, are the amplification bandwidth of the detected signals and the scanning rate of the beam deflection apparatus of the confocal scanning microscope.

In very particularly advantageous fashion, to prevent saturation of the excitation of fluorescing materials at a single specimen point, provision is made for simultaneous illumination or excitation of multiple specimen regions. In this fashion, the excitation light output made available by the light source to the multi-photon light source can be distributed simultaneously to multiple specimen points, so that the fluorescing materials located there are simultaneously excited to fluoresce. This requires a corresponding simultaneous detection of these different specimen regions, which can be achieved with corresponding illumination and detection methods known from the existing art. For example, illumination of multiple focal points or specimen regions could be carried out by means of a rotating micro-lens wheel, as known from DE 196 53 413 or EP 0 753 779. Alternatively, illumination could be performed with a reflective disk scanner, as is known from DE 44 37 896 C1. For detection of the specimen points excited by an arrangement of this kind, in the simplest case a planar detector could be used. With multi-photon excitation, one or more confocal detection pinholes can be dispensed with; the reason is that multi-photon excitation can occur only in the focal region of the microscope objective, since only there is the excitation output of the light source high enough. As an alternative to illumination with multiple focal points, provision could be made for illumination with a focal line, for example using a slit-shaped illumination and detection system. In this context, however, the resolution capability is confocal only perpendicular to the focal line; the resolution existing along the focal line is the same as that available in conventional microscopy.

Fluorescent dyes, caged compounds, and/or nanocrystals could be used as fluorescing materials. These are fluorescing materials that are commonly used in the biomedical field and in the field of biological and biochemical basic research; biological specimens can be specifically bound to the fluorescing materials using, for example, antibody bonds to complementary specimen regions.

With regard to the light sources and various illumination modes provided for the apparatus, to avoid repetition the reader is referred to the portion of the specification relevant to the corresponding method step.

BRIEF DESCRIPTION OF THE DRAWINGS

There are various ways of advantageously embodying and developing the teaching of the present invention. In conjunction with the explanation of the preferred exemplary embodiments of the invention with reference to the drawings, an explanation is also given of generally preferred embodiments and developments of the teaching. In the drawings.

DETAILED DESCRIPTION OF THE INVENTION

Figure 1:
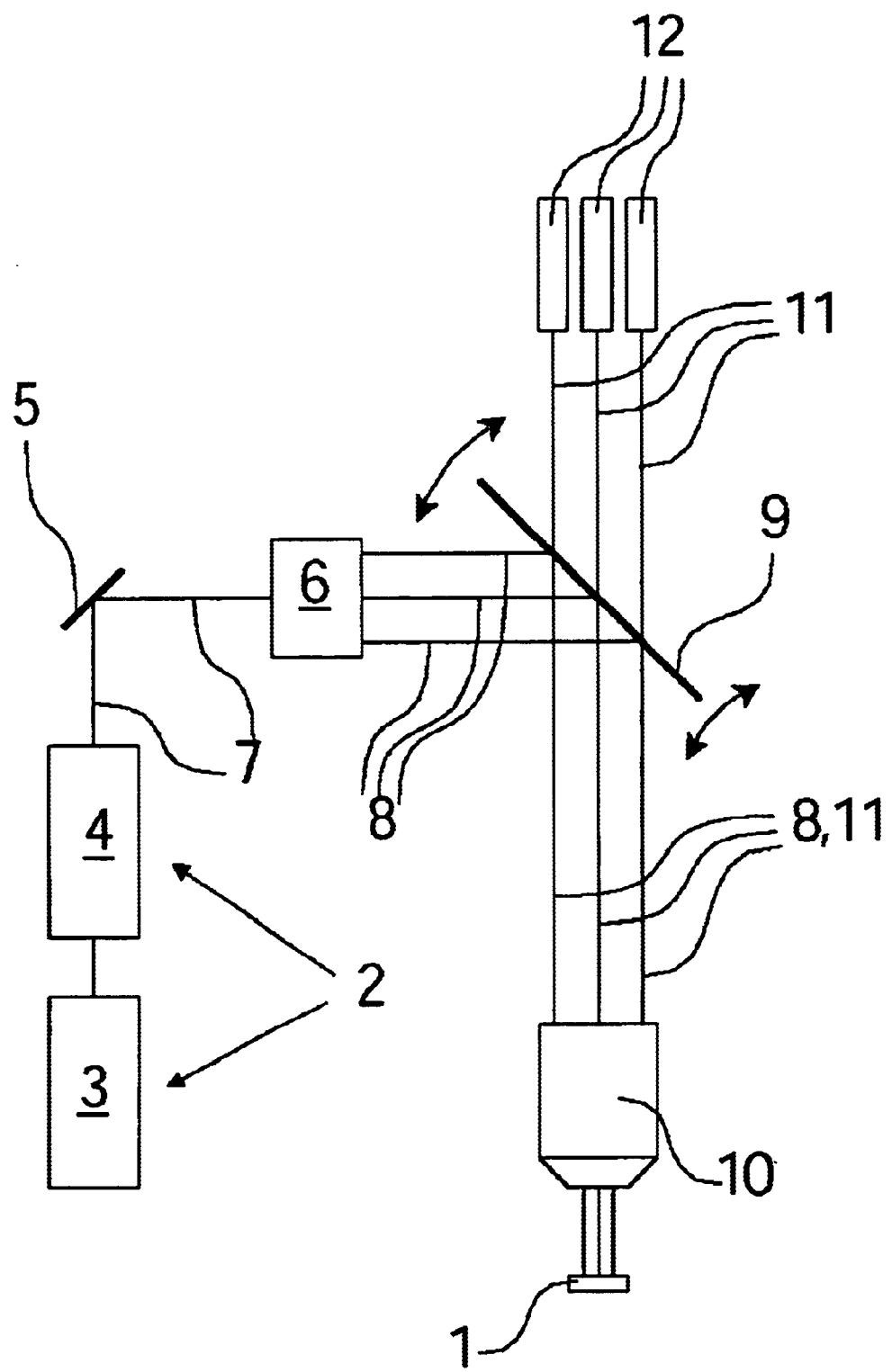
FIG. 1 schematically depicts a first exemplary embodiment of an apparatus according to the present invention.
Figure 2:
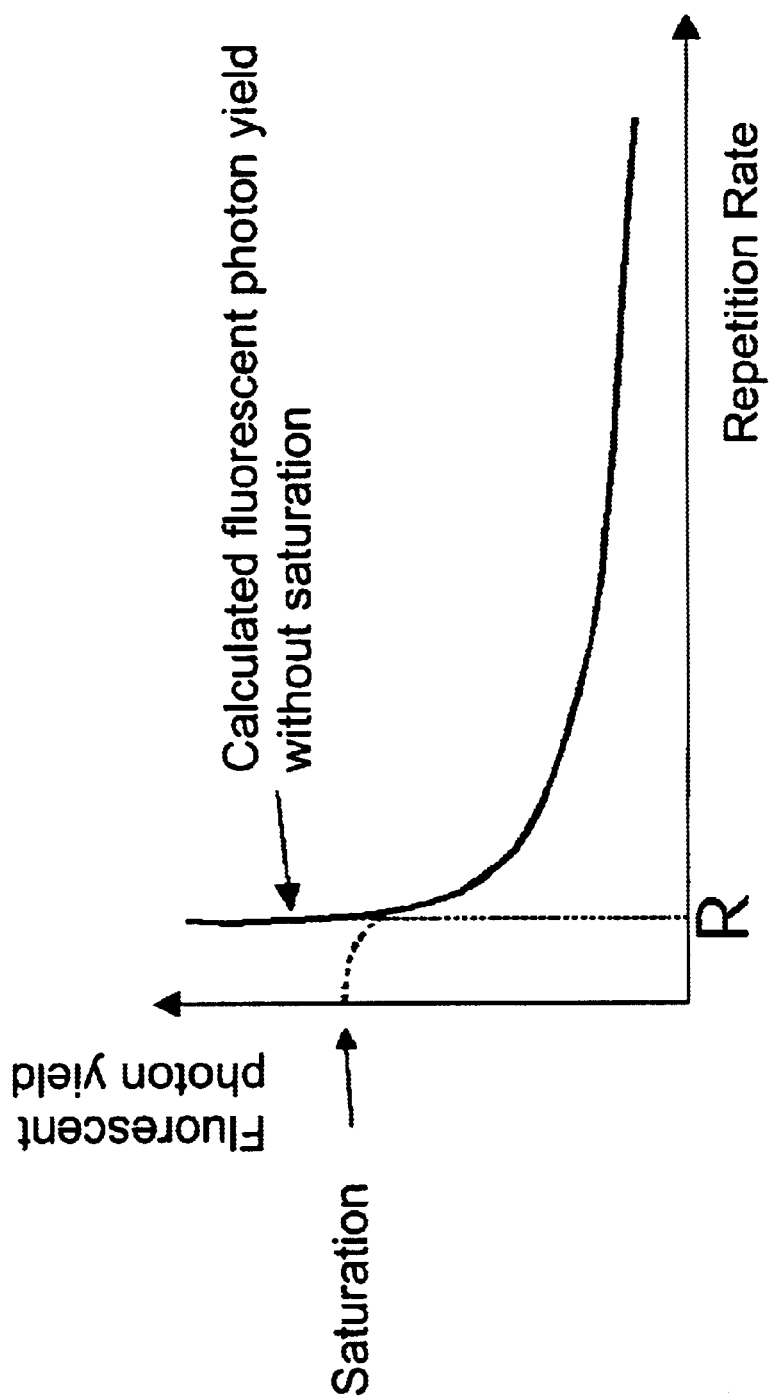
FIG. 2 shows a diagram in which the fluorescent photon yield is plotted as a function of the repetition rate.

For optimum fluorescent photon yield, the operating parameters of light source 2 causing the multi-photon excitation, and the system parameters of the confocal scanning microscope, are adapted to the properties of the fluorescing materials. The pulse repetition rate of light source 2 is defined according to the diagram of FIG. 2. In this diagram, the fluorescent photon yield is plotted as a function of pulse repetition rate, for a constant average light output of light source 2. The fluorescent photon yield is plotted on the diagram as a bold solid line. Because of the phenomenon of saturation of the fluorescing materials, the fluorescent photon yield cannot be arbitrarily increased at a lower repetition rate and thus at a higher pulse output (the average light output of light source 2 being constant), and the maximum attainable fluorescent photon yield is therefore plotted as a dashed line. A decrease in the pulse repetition rate beyond the value R, and thus an increase in the output of a pulse, would accordingly not bring about any increase in the fluorescent photon yield, so the pulse repetition rate of light source 2 is set to the value R.

Light source 2 comprises a titanium:sapphife laser 3 and a regenerative amplifier 4 downstream from titanium:sapphire laser 3.

The light emitted from light source 2 is directed, after reflection at mirror 5, onto beam divider 6. Beam divider 6 divides illuminating light beam 7 into three partial illuminating beams 8. Scanning mirror 9, mounted tiltably and configured as a dichroic beam splitter, reflects the three partial illuminating beams 8 and deflects them as a result of the tilting, so that specimen 1 can be scanned by the deflection of scanning mirror 9. The deflection of scanning mirror 9 is accomplished in two directions substantially perpendicular to one another, only one of which is drawn. As a result of the division of illuminating light beam 7 into three partial illuminating beams 8, after focusing of the three partial illuminating light beams 8 by microscope objective 10, three specimen regions are simultaneously illuminated and the fluorescing materials located there are excited to fluoresce.

Fluorescent light 11 emitted from the three simultaneously illuminated specimen regions, which is collected by microscope objective 10, passes as a result of its wavelength through the dichroic beam splitter configured as scanning mirror 9 and can be detected by the three detectors 12.

The fluorescing materials used for two-photon excitation are fluorescent dyes that are specifically bound to individual specimen regions of specimen 1.

In conclusion, be it noted very particularly that the exemplary embodiments discussed above serve merely to describe the teaching claimed, but do not limit it to the exemplary embodiments.

What is claimed is:

1. A method for the detection of fluorescent light in scanning microscopy comprising the steps of emitting light from a light source so as to provide an illuminating light beam, dividing the illuminating light beam into a plurality of partial illuminating beams so as to illuminate multiple specimen regions simultaneously, exciting fluorescing materials in a specimen region by means of multi-photon excitation, adapting operating parameters of a light source for optimum fluorescent photon yield to the properties of the fluorescing material in the specimen region, wherein the light source causes multi-photon excitation, and detecting fluorescent light of the specimen regions simultaneously.

2. The method as defined in claim 1, wherein an adaptation is made to the lifetime of the excited states of the fluorescing materials.

3. The method as defined in claim 1, wherein the light emitted by the light source is pulsed light and the duration of the emitted light pulses by the light source is correspondingly adjusted.

4. The method as defined in claim 1, wherein the light emitted by the light source is pulsed light and the pulse repetition rate of the light emitted by the light source is correspondingly adjusted.

5. The method as defined in claim 1, wherein the wavelength of the light emitted by the light source is correspondingly adjusted.

6. The method as defined in claim 1, wherein the dynamic range of the detector system of the scanning microscope is correspondingly adjusted.

7. The method as defined in claim 1, wherein a rotating micro-lens wheel or a reflective disk scanner is used for illuminating multiple specimen regions simultaneously with multiple focal points.

8. The method as defined in claim 1, wherein a slit-shaped illumination system is used for illuminating multiple specimen regions simultaneously with a focal line.

9. The method as defined in claim 1, wherein fluorescent dyes, caged compounds, and/or nanocrystals are used as fluorescing materials.

10. An apparatus for the detection of fluorescent light comprising:

a scanning microscope with a light source for generating an illuminating light beam means for dividing the illuminating light beam into a plurality of partial illumination light beams so as to illuminate multiple specimen regions simultaneously, means for exciting fluorescing materials in the multiple specimen region by means of multi-photon excitation, means for adapting operating parameters of the light source for optimum fluorescent photon yield to the properties of the fluorescing material in the specimen region, wherein the light source causes multi-photon excitation, and means for detecting fluorescent light of the specimen regions simultaneously.

11. The apparatus as defined in claim 10 wherein the light source consists essentially of a mode-coupled laser system, and the mode-coupled laser system includes at least one of a titanium:sapphire laser, a semiconductor laser, a flash lamp-pumped laser, an optically parametric oscillator, and an optically parametric amplifier.

12. The apparatus as defined in claim 10, wherein the means for dividing the illuminating light beam is a rotating micro-lens wheel or a reflective disk scanner for the illumination of multiple focal points.

13. The apparatus as defined in claim 10, wherein the means for dividing the illuminating light beam is a slit-shaped illumination system which is used for illumination of a focal line.

14. An apparatus for the detection of fluorescent light comprising:

a confocal scanning microscope with a mode-coupled laser source for generating an illuminating light beam, means for generating a plurality of partial illuminating light beams from the illuminating light beam for illuminating multiple specimen regions simultaneously, means for exciting fluorescing materials in the multiple specimen regions by means of multi-photon excitation, wherein a regenerative amplifier is arranged downstream from the mode-coupled laser; and means for adapting operating parameters of the mode-coupled laser for optimum fluorescent photon yield to the properties of the fluorescing material in the specimen region, wherein the mode-coupled laser causes multi-photon excitation.

15. The apparatus as defined in claim 14, wherein means for detecting simultaneously fluorescent light from the specimen regions is provided.

16. The apparatus as defined in claim 14, wherein the mode-coupled laser system, includes at least one of a titanium:sapphire laser, a semiconductor laser, a flash lamp-pumped laser, an optically parametric oscillator, and an optically parametric amplifier.

17. The apparatus as defined in claim 14, wherein the means for generating a plurality of partial illuminating light beams is at least one of a rotating micro-lens wheel and a reflective disk scanner.

* * * * *